US006679913B2

United States Patent
Homsy

(10) Patent No.: US 6,679,913 B2
(45) Date of Patent: *Jan. 20, 2004

(54) IMPLANTABLE SHEET MATERIAL

(75) Inventor: Charles Homsy, Nyon (CH)

(73) Assignee: Tranquil Prospects Ltd., Tortola (VG)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/291,443

(22) Filed: Apr. 13, 1999

(65) Prior Publication Data

US 2002/0082707 A1 Jun. 27, 2002

(30) Foreign Application Priority Data

Apr. 14, 1998 (EP) ............................................. 98810317

(51) Int. Cl.⁷ .................................................. A61F 2/02
(52) U.S. Cl. .............................. 623/11.11; 623/23.51; 606/151
(58) Field of Search ........................ 623/11.11, 16.11, 623/23.51, 23.76; 606/151

(56) References Cited

U.S. PATENT DOCUMENTS

| 3,761,402 A | | 9/1973 | Atwood | 208/314 |
| 3,971,134 A | * | 7/1976 | Bokros | 132/201.1 |
| 3,992,725 A | | 11/1976 | Homsy | 3/1 |
| 4,073,999 A | * | 2/1978 | Bryan et al. | 428/311 |
| 4,118,532 A | | 10/1978 | Homsy | 428/294 |
| 4,156,943 A | * | 6/1979 | Collier | 623/16.11 |
| 4,849,285 A | | 7/1989 | Dillon | 428/330 |
| 5,037,445 A | * | 8/1991 | Sander et al. | 623/66 |
| 5,300,115 A | * | 4/1994 | Py | 623/4 |
| 6,113,640 A | * | 9/2000 | Tormala et al. | 623/18 |

FOREIGN PATENT DOCUMENTS

| EP | 051 955 A2 | 5/1982 |
| FR | 2138735 | 1/1973 |

* cited by examiner

*Primary Examiner*—Paul B. Prebilic
(74) *Attorney, Agent, or Firm*—Seed IP Law Group Ltd.

(57) ABSTRACT

The biocompatible material has a resilient, porous structure and is suitable for in vivo implantation. It possesses pores of a narrow pore size distribution between 150 to 300 μm and is usable for forming a sheeting with a thickness of less than 0.8 mm for tissue reinforcement or which is usable for forming shapes for soft tissue augmentation and with an improved tensile strength. The material provides an environment in which normal tissue growth is fostered. The material has a porous structure comprising fibers or particles having a critical surface tension of 35 mN/m or higher. The material has a porous structure of alumina fibers or particles and PTFE resin fibers and particles bonded together by sintered polytetrafluoroethylene in a manner to expose a maximum amount of fiber surface. The method of preparing the material includes the steps of mixing, filtering, compressing, rolling, sintering, drying, sintering and leaching or solving of leachable or solvable material.

15 Claims, No Drawings

IMPLANTABLE SHEET MATERIAL

The present invention relates to implantable materials which can be formed into sheets of less than 0.8 mm for tissue reinforcement or into formed shapes for soft tissue augmentation. These materials have sufficient strength for the respective implantation applications. When implanted in a body the material promotes ingrowth of normal body tissue, and thereby becomes linked to adjacent tissue, and ultimately becomes filled with tissue. Thus, the materials may function in and of themselves or can stabilize appliances upon which they may be bonded; as, for example, to polymers for skeletal defect filling, to tendon replacements to which the materials are bonded at each end for securing the tendon replacement, to an implantable wear material for joint resurfacing applications or to other prosthetic joint implants for knee, hip and other skeletal joints.

U.S. Pat. No. 3,992,725 describes a composition of material suitable for in vivo implantation. It has a resilient, fibrous, porous structure; at least a portion of the biocompatible fibers of said structure have a critical surface tension above 35 mN/m on a scale extending from 20 to 80 mN/m. The structure includes biocompatible means for bonding said fibers into the porous structure having substantial interconnected spaces between the fibers. The structure possesses sufficient resiliency and distensibility when implanted to develop the type of ingrowth tissue needed at the implant location responsive to the mechanical forces at the implant site.

The typical formulation of said material was taught to be 80 vol % sodium chloride, 10 vol % carbon fibers, 6 vol % PTFE polymer fibers, and 4% PTFE particulate resin. The carbon fibers in the finished material (which is 80% porous because of the dissolving out of the sodium chloride component) provide the "portion of the fibers of said structure" having a surface tension greater than 35 mN/m. In effect the carbon fibers became very short during the manufacturing process, and became a dispersed particulate coating over a portion of the PTFE fibers. This formulation became widely used for surgical implantation.

Alternative fibrous materials to the carbon fibers are disclosed: Zirconia (zirconium oxide) fibers, Alumina (aluminum oxide) fibers, "whiskers" of either alumina or zirconia, stainless steel wire.

The teachings and associated method of preparation of U.S. Pat. No. 3,992,725 yielded useful materials of 78–82% porosity with pore size range between 10 and 600 $\mu$m (at col. 2, lines 58–60 of the patent). This pore size distribution resulted from the use of the fugitive salt ingredient having particle diameters between 10 and 600 $\mu$m. These materials exhibited bulk properties of a stiff sponge in thicknesses greater than a few mm. Their properties allowed them to become widely used for augmenting the bony profile of the facial skeleton. In sheet form the products did not have strength useful for implantation applications at thickness less than about 0.8 mm; the stiff sponge-like bulk properties prevented use in direct soft tissue augmentation such as for cheek area and post-mastectomy breast reconstruction.

An object of the present invention is to provide an improved implantable composition of material which not only promotes ingrowth of normal body tissue, but has also an excellent tensile strength if a sheeting of a thickness of less than 0.8 mm, e.g. about 0.5 mm, is formed and/or, if formed into a monolithic shape, has the bulk properties of a soft sponge.

Further required properties of such a composition are:
suitability for stabilizing prostheses of biocompatible substances such as metal, polymers or elastomers
suitability in soft tissue augmentation
suitability for use in orthopedic rebuilding of joints and parts thereof
heat resistance, so that it can be sterilized by the usual steam autoclave procedures without being adversely effected thereby
suitability for implantation in a joint in that it is highly wear resistant and has low friction properties
capability of promoting ingrowth of tissue and being not sequestered by fibrous tissue when implanted.

Still a further object is to provide an improved method of making such an implantable material.

Many years of experimentation showed that about 82% porosity was the upper limit possible to prepare materials of useful mechanical integrity. Although sheeting from the prior art material as thin as 0.6 mm had been made, it was typically very fragile and therefore not commercially interesting.

Now it has been unexpectedly discovered that useful higher porosity (87%) and much softer products for soft tissue replacement, on the one hand, and about 0.4–0.5 mm high strength sheeting for tissue reinforcement, on the other, could be prepared if the particle size of the fugitive ingredient, salt, is selected to be narrow, in the range 150 to 300 $\mu$m. This yields the equivalent narrow pore size distribution in the products. The ultimate tensile strength of 1 mm thick sheeting is increased from about 300 N/cm$^2$ to 600 N/cm$^2$ by reducing the pore size range to 150–300 $\mu$m from 10–600 $\mu$m.

It has also been surprisingly found that further enhancement of the tensile strength of the very thin 0.4–0.5 mm sheeting can be achieved by adding a second sintering step after the desired thickness of the sheeting has been obtained by a sanding process. These extra sanding and sintering steps would follow the sintering step (f) of the U.S. Pat. No. 3,992,725. The strength of such sheeting is about 300 N/cm$^2$. This means that the tensile strength is doubled in relation to prior art products.

| Thickness (cm) | Tensile strength (mean) | |
| --- | --- | --- |
| 0.122 | 289.79 | prior art |
| 0.096 | 576.66 | Narrow distribution of pore size |
| 0.039 | 379.33 | Narrow distribution of pore size and double sintering |

Thus, the inventor of the present invention has found that greatly improved product properties have resulted from two unexpectedly simple modifications to the process:
(A) a relatively narrow pore size distribution in the range of 150–300 $\mu$m; and
(B) an additional sintering step when preparing sheeting at a thickness less than about 0.8 mm.

These and other objects and advantages are hereinafter set forth and explained.

DESCRIPTION OF THE PREFERRED EMBODIMENTS

The preferred material for tissue ingrowth consists of sintered polytetrafluoroethylene with alumina particles and substantial void space with a pore size distribution in the range of 150–300 $\mu$m. The polytetrafluoroethylene material has been used for implantable devices and has been found to be biocompatible, that is, it does not produce any inflammatory response by the host tissue. The preferred material to be used is marketed by Du Pont Co. as TEFLON TFE. High purity alumina powder (Type RC-HP-DBM) has also been found to be biocompatibile and was obtained from Malakoff Industries, Richmond, Va., 23261. This product has the desired particle size of approximately 0.5–1.5 microns.

With implanted materials the relative surface energy or wettability has an effect on the manner in which the tissue responds. Tissue element attachment to the surface of an implanted material can be substantially reduced by decreasing the surface energy or reducing the wettability. Such low surface energy materials are generally sequestered in fibrous tissue.

Since the polytetrafluoroethylene (hereinafter PTFE) material has low surface energy, the promotion of ingrowth of normal body tissues will be aided if the surface energy can be increased. Also, for such ingrowth the composition of material should contain substantial void space.

It is well known that cellular elements of tissue exhibit a degree of electrical polarity. Consequently electrostatic adhesion of cellular elements to the surface of an implanted material is minimized when the implanted material itself exhibits very low surface energy (low critical surface tension), that is, electrostatic attractive force. The implantation products of prior art have taken advantage of the bio-compatibility of PTFE material and the polymeric properties of this material as these relate to the development of highly porous structures, and at the same time have recognized desirability of fostering tissue ingrowth and attachment to the implant material by providing a substantial quantities of alumina of surface area which exhibits a relatively high surface energy for electrostatic attraction of tissue elements. In the preferred form of the present invention this is achieved by incorporating substantial quantities of alumina surface tension on the order of 50 mN/m. In this way an implant structure is provided which presents to cellular and tissue elements, a substantial percentage of surface exhibiting relatively high critical surface tension.

The preferred composition of material of the present invention is made by intimately mixing in the proportions hereinafter set forth alumina particles and PTFE, both particles and fibers. The preferred amounts of PTFE fibers to resin is preferred to be greater than 1 to 2 and less than 2 to 1. The PTFE fibers are preferred to have a strand length up to about 5 cm.

In order to help provide the desired void space, a material which is soluble in a suitable solvent is added to the above mixture in an amount to produce the desired amount of void space in the material, preferably in the range from 70 to 87%, of the volume of the finished material. If water is to be the solvent, the soluble material may be common material such as sodium chloride crystals of particle size in the narrow range between 150 and 300 μm.

Alternatively other soluble material/solvent combinations may be used. For example, when water is to be the solvent, soluble materials may be selected from the group of water soluble salts which are thermally stable at temperatures below about 370° C. Such salts could be sodium carbonate, calcium fluoride, magnesium sulfate, and others. It will generally be preferred to use the sodium chloride-water system since the sodium chloride would be completely compatible in the body, in the event small amounts were left in the material from the leaching step hereinafter described.

A typical formulation would include 80% sodium chloride of a narrow particle size range of 150–300 microns, 1.13 vol. % alumina particles, 10 vol % PTFE resin fibers, and 8.6 vol % PTFE resin particles.

| | |
|---|---|
| Alumina fibers | 0.5% to 2.5% by volume |
| Resin fibers | 5% to 20% by volume |
| Resin particles | 5% to 15% by volume |
| Soluble material | 89.5% to 62.5% by volume |

The steps involved in preparing these materials are as follows:

a) Mixing: In this step the polymer and the alumina and soluble ingredients are suspended in a suitable organic solvent such as purified isoparaffinic solvent. It is preferred that aromatic content of such solvent be less than 1% by weight. The resulting slurry is mixed at a very high speed in a high shear mixer such as a Waring blender. The proportion of solvent to dry ingredients is important, and must be adjusted to the size of the mixer used. The total volume of our mixer is 1000 milliliters and 500 milliliters of solvent are used for dry ingredient weights on the order of 100–150 grams. Mixing is carried out for between one and five minutes, depending upon the particular ingredients used.

b) Filtration: The mixed slurry is rapidly poured into a vacuum filter such as a Buchner funnel, and filtration proceeds from between a few seconds to several minutes, depending upon ingredients used. The residual solvent left in the filter cake is carefully monitored so as to be less than about 20% by weight.

c) Compression: The filter cake from step (b) is placed within the platens of a heated press (50° C.–80° C.) and compression is applied at levels of between $3.45 \cdot 10^5$ Pa–$2.07 \cdot 10^7$ Pa for between one and five minutes, again depending upon the particular ingredients. The present residual solvent in the filter cake after compression is routinely monitored and conditions are adjusted so that the level of solvent is between six and sixteen weight percent.

d) Rolling: The compressed filter cake from step (c) is run through the nip of heated rolls such that the thickness of the cake is reduced in decrements of approximately 0.05 cm to levels of between 1.5–1.0 mm. The temperature of the heated rolls should be in the range of 380° C. through 138° C. That is, heated rolls over this temperature range are required in order to help volatilize the carrier solvent. Moreover, during this step each pass through the rolls is made perpendicular to the direction of the previous rolling maneuver.

e) Drying: Stock material is dried to evaporate any residual solvent by placing it in an oven kept at temperatures of between 150 and 177° C. for approximately 8 hours usually.

f) Sintering: The dried stock is now sintered. Sintering is carried out in a heated press at temperatures between 320° C. and 360° F. and a pressure between $3.45 \; 10^5$–$3.45 \; 10^7$ Pa for periods of time from 1 to 30 minutes depending upon the thickness of stock. Alternately sintering may be carried out by heating the stock material to temperatures between 320° C. and 360° C. for periods extending to several hours.

f') Sanding (optionally): For obtaining the desired thickness of the sheeting of the stock of preferably 0.4–0.5 mm f'') Second sintering (optionally) under the same conditions as in step f.

g) Leaching: The stock is leached to dissolve out water soluble filler material by placement in a container containing purified water and thereby develop discrete volume and porosity. Purified water is caused to flow at a slow rate through such container in order to provide the maximum driving force for diffusion of dissolved filler from the stock into a leaching water. The leaching step is usually allowed to proceed for 48 to 96 hours depending on the thickness of the product (0.4–10 mm). Longer times would probably be required for thicker stock. The purified water is preferred to be warm to increase the rate of dissolving of salt.

h) Drying: The leach stock is then placed in an oven held at a temperature between about 710° C. and 177° C. in order to affect drying of the residual water contained within the stock material. The drying step may include a 24-hour hold at 150° C. to volatilize any residual solvent.

The product material from the above series of steps exhibits several important properties of significance to tissue ingrowth. During the leaching step the voids are created in the material. The narrow range of particle size of the fugitive salt is responsible for the surprising improvement of the mechanical properties of the material. A portion of the voids have a spherical shape as they are formed by the leaching of generally spheroidal sodium chloride crystal from the material. In addition, the material which is produced as described also develops dendritic voids which interconnect in random fashion with the spheroidal voids to thereby provide a particularly effective open structure for the ingress and egress of body fluids necessary for the development and maturation of tissue within the voids. The strength of a stock in the form of a sheeting with a thickness of 0.4 to 0.5 mm is about 300 N/cm$^2$.

Further the material immediately surrounding these voids presents in part the relatively high surface tension of the alumina particles which are fused to the surface of the PTFE resin fibers, said fibers being bonded together by the PTFE resin particles to provide a material having necessary structural integrity after the leaching step removes the soluble material.

It is believed that with the development and maturation of tissue within such voids, such tissue is not as vulnerable to infection as prior implants since substantial blood supply is developed to allow the normal body functions for fighting infection to be active within such material. In prior materials for implants, the appearance of an infection in connection with an implanted device generally necessitated the removal of the device if the normal body infection fighting mechanisms were not able to reach the infected area.

Additionally, because of the resiliency and distensibility of this composition of material, the tissues developing therein feel or are subjected to the normal mechanical forces at the sites of the implant which assist in the formation of the type of tissue needed at such location.

The improved compositions of material, because of their improved strength and because they promote the ingrowth of normal body tissue can be considered for a wider range of applications: soft tissue defect reinforcement and soft tissue augmentation, hard tissue augmentation and partial or complete joint prostheses, birth control by vas deferens or Fallopian tube blockage from implant material, tendon and ligament prosthesis fixation and replacement, and other implant procedures.

It has been found that wider range of applications is possible by combining the narrow particle size range of the soluble filler with varying amounts of the other ingredients. Also, the combination of alumina and PTFE is adjusted to provide a balance of mechanical behavior and surface energy.

In the formation of the material the rolling proceeds until the thickness of the material is on the order of 1.0–1.5 mm., thick to thereby provide a maximum strength. When thicker stock is desired, particularly for soft tissue augmentation, it can be achieved by following the above steps (a), (b), (c), (d) and (e) and then stacking the dried stock to the desired multiple of the single ply thickness. The stacked layers are sandwiched between aluminum foil and placed within the platens of a press held at a temperature of 327° to 366° C. Pressure is applied gradually over one to two minutes depending on the area of the laminate to a final hold pressure of 6.81·10$^6$ Pa. This hold pressure is maintained for a period of time equal to the number of layers times five minutes, and may not need to exceed fifteen minutes. This laminated stock is then leached and dried as set forth in steps (g) and (h) above.

Specific preferred formulations include the following formulations all of which are prepared with said fugitive ingredient, sodium chloride, of narrow particle range of 150–300 microns":

| Formulation | Alumina particles (Vol% Percentages) | Resin fibers (Vol% Percentages) | Resin particles (Vol% Percentages) | Salt (Vol% Percentages) |
|---|---|---|---|---|
| A | 0.62 | 6.1 | 5.8 | 87.5 |
| B | 1.67 | 14.8 | 12.7 | 71 |
| C | 1.13 | 10 | 8.6 | 80 |

Formulation A has been found for soft tissue replacement as in post-mastectomy reconstruction wherein the desired shape of the reconstruction is formed in the formulation A material as described herein; it has also been effective in augmentation of the supple tissue of the cheek area. It provides sufficient natural aesthetic softness and becomes fixed at its implanation locus by tissue ingrowth.

Formulation B has application for repaired tissue reinforcement as in the case of herniation repairs, abdominal incisions, thoracic wall re-approximations and for defect obliteration as in dura mater replacement over the brain, and for certain hand and wrist surgery wherein the material functions as an interface between gliding tissue structures. In the latter two applications, it may be used as a lamination to a suitable polymer or elastomer. It may also be used in sandwich constructions with suitable metallic fabrics for certain repaired tissue reinforcement. This formulation provides necessary tensile strength at sheeting thicknesses as low as 0.4 mm.

Formulation C finds use mainly in facial boney profile augmentation where it is implanted as an onlay at the locus of profile distortion.

The above ingredients were suspended in approximately 700 milliliters of isoparaffinic solvent and agitated in a Waring blender for 1–2 minutes. Mixed ingredients were rapidly poured into a Buchner funnel and suction applied for approximately one minute. The filter cake thereby obtained was placed within the platens of a heated press (660 C) and compressed under 3.45·10$^6$ Pa for one minute. A level of isoparaffinic solvent within the product at this stage was measured to be 11.5 weight percent. The product was then rolled according to the procedure described under step d above with roll temperature of 41 C. The rolled stock was dried for 8 hours and 150 C and then compression sintered under 3.45·10$^6$ Pa for six minutes at 350° C. This product is now suitable for processing into finished product according to the subject disclosure. For example, lamination to fluorinated ethylene propylene polymer in a heated platen press at 300 C. under 6.9 10⁴ Pa pressure for five minutes.

While the foregoing sets forth the preferred material composition of the present invention, other materials may be used. Any chemically stable perfluorinated high polymer such as polyhexafluoropropylene or a copolymer of hexafluoropropylene and tetrafluoroethylene, which is commercially available as the TEFLON FEP resin from Du Pont, is believed to be suitable base material from which a porous implantable material may be formed. Other suitable materials are high molecular weight polyethylene containing no additives, polyester polymers such as polyethylene terephthalate. The preferred materials to be used have the following characteristics: they are biocompatible (suitable for in vivo implantation). They are not subject to chemical migration when implanted; they are stable for autoclaving; they allow development of porosity for ingrowth and they are resilient.

For example polyester fibers as sold by Du Pont Company under their mark DACRON can be used. A typical formation includes 4.5 grams of graphite fibers, 2.52 grams of the above-mentioned polyester fiber flock, 2.76 grams of TEFLON TFE-6 resin and 52.1 grams of salt. This formulation was mixed, filtered and otherwise processed in accordance with the steps set forth above except that the compression sintering was carried out for one minute at 276° C.

While it is preferred that the additive is alumina particles, a combination of filamentary and powdered carbon or metal (which metals are suitable for implantation) or other fibers such as ceramic, may be used as additives, provided the internal surface tension of the material remains sufficiently high to be highly blood wettable and therefore suitable for ingrowth of tissues.

Following are examples of other material compositions of the present invention.

| Ingredients | Volume % | Grams |
|---|---|---|
| Salt, NaCl | 80% | 6.2 g |
| Zirconia Fibers | 105% | 2.00 g |
| TEFLON TFE Fiber | 6% | 0.50 g |
| TEFLON TFE - 6 Resin | 4% | 0.33 g |

The zirconia fibers used were obtained from the Mond Division of Imperial Chemical Industries and are sold under the trademark SAFFIL. They 5 are based on zirconium oxide. The fiber diameter is 3±2 micra.

| Ingredients | Volume % | Grams |
|---|---|---|
| Salt, NaCl | 80% | 6.2 g |
| Alumina Fibers | 105 | 1.00 g |
| TEFLON TFE Fiber | 6% | 0.50 g |
| TEFLON TFE - 6 Resin | 4% | 0.33 g |

The alumina fibers used were SAFFIL alumina fibers based on aluminum oxide

| Ingredients | Volume % | Grams |
|---|---|---|
| Salt, NaCl | 80% | 34.72 g |
| Whiskers SiC, Al₂O₃ | 10% | 7.2 g |
| TEFLON TFE Fiber | 6% | 2.76 g |
| TEFLON TFE - 6 Resin | 4% | 1.84 g |

| Ingredients | Volume % | Grams |
|---|---|---|
| Salt, NaCl | 80% | 34.72 g |
| Whiskers SiC, Al₂O₃ | 8 | 5.76 g |
| TEFLON TFE Fiber | 6% | 3.22 g |
| TEFLON TFE - 6 Resin | 4% | 2.3 g |

The single crystal filaments (whiskers) of silicone carbide and aluminum oxide may be purchased from General Technology Corporation Reston, Va. as Type 6B and falling in the range from 2 to 30 micra in diameter and from 20 to 1000 micra in length.

| Ingredients | Volume % | Grams |
|---|---|---|
| Salt, NaCl | 80% | 34.72 g |
| Stainless Steel Wire | 10% | 16.0 g |
| TEFLON TFE Fiber | 6% | 2.76 g |
| TEFLON TFE - 6 Resin | 4% | 1.84 g |

| Ingredients | Volume % | Grams |
|---|---|---|
| Salt, NaCl | 80% | 34.72 g |
| Stainless Steel Wire | 8% | 12.8 g |
| TEFLON TFE Fiber | 6% | 3.22 g |
| TEFLON TFE - 6 Resin | 4% | 2.2 g |

The stainless steel wire used was approximately one-fourth inch (5 to 6 mm) in length and 0.005 inches (0.127 mm) in diameter.

| Ingredient | Volume % | grams |
|---|---|---|
| Salt NaCl | 80% | 34.72 |
| Vitreous Carbon Fiber | 10% | 3.0 |
| Polyester Fiber | 10% | 2.7 |

| Ingredient | Volume % | grams |
|---|---|---|
| Salt NaCl | 80% | 34.72 |
| Vitreous Carbon Fiber | 10% | 3.0 |
| Polyaramide Fiber | 10% | 2.7 |

The polytetrafluoroethylene fiber, polyester fiber and the polyaramide fibers were obtained from DuPont Company of Wilmington, Del. under the trademarks TEFLONM DACRON AND NOMEX, respectively.

Further, it has been found that in the above polyester and polyaramide compositions, extensive mixing is used to provide a complete blending of the components to avoid the production composition in which not all of the fibers were completely integrated into the structure. To avoid extensive mixing, the following composition was made:

| Ingredient | Volume % | grams |
|---|---|---|
| Salt NaCl | 80% | 34.72 |
| Vitreous Carbon Fiber | 10% | 3.0 |
| Polyester Fiber | 6% | 1.65 |
| TEFLON TFE - 6 Resin | 4% | 1.84 |

As can be seen this composition is substantially the same as the previously described composition with the addition of the polytetrafluoroethylene resin. This resin is believed to act as a mixing adjuvant allowing the polyester fibers and the alumina paticles to be mechanically mixed or blended with the salt and a liquid organic solvent to form a substantially homogeneous mixture. While improved compositions may be produced without the inclusion of such mixing adjuvant, its inclusion greatly simplifies the production of a suitable composition.

Also a high molecular weight polyethylene resin such as the resin sold by Hercules, Inc., of Wilmington Del., under the trademark HYFAX 1900 was used with the polyester and polyaramide fiber compositions in place of the polytetrafluoroethylene and as a strengthening ingredient. Such compositions were sintered at a temperature of 232° C.

From the foregoing it may be seen that the improved composition of the present invention may be of a wide variety of materials provided such materials are biocompatible, utilize a fugitive ingredient (salt) with a particle size range of 150–300 microns and produce a fibrous, porous structure in which at least a portion of the fibers have a critical surface tension within the preferred range so as to be blood wettable and thereby assure the promotion of ingrowth of living tissue when implanted in a human body.

The composition includes an ingredient (as for example, alumina particles) which supplies the elevated critical surface tension, polymer fibers which are bonded into a pliant, resilient, and strong porous composition with a suitable fugitive material such as salt providing the controlled degree and size of porosity by initially being incorporated in the structure and being leached therefrom after the sintering.

As has been shown, the components which supply the body fluid wettability may be selected from the group of particulate or fibrous biocompatible materials such as vitreous carbon, stainless steel, silicon carbide, ceramics such as aluminum oxide, calcium phosphate tribasic and zirconium oxide, and other materials which are biocompatible provided these have the required high critical surface tension and may be sterilized with accepted procedures.

The bonding material may be polytetrafluoroethylne, polyester, polyethylene, polyaramide, and other materials which are biocompatible, will bond the fiber materials and may be sterilized in conformity with accepted operating room procedures.

The improved composition of material of the present invention forms a three dimensional structure which is substantially isotropic or has substantially uniform characteristics in all three dimensions. The composition of material further has a sufficient resiliency and distensibility so that on implantation the tissues growing therein are subjected to the forces at the site of the implant and will tend to mature into the type of tissue needed at such location responsive to such forces.

In all the above compositions which differed from the preferred composition, the previously described steps in the method of producing the preferred compositions were used with only a variation in temperature used to accommodate the different bonding materials. For example, sintering temperatures for the polyester binding material would be approximately 345° C. for the polyaramide material.

The stabilization of orthopedic appliances can be accomplished by the bonding of the material of the present invention to the fixation portion of the appliance. A typical example of this stabilization is the bonding of the ingrowth promoting material to the stem of a metal femoral head prosthesis. Also such material can be added to the convex surface of a metal acetabular prosthesis The bonding to a metal prosthesis may be accomplished preferably by bonding a thin layer of fluorinated ethylenepropylene (Du Pont TEFLON FEP) to the material before the major portion of the salt is leached therefrom. The salt on such a surface is removed before bonding the binding layer thereto. This may be accomplished by floating the material on distilled water for a short period of time to assure that the bonding material is bonded to the composition of material. Such a bonding layer provides the bond to the metal prosthesis.

It is preferred to bond the materials of the present invention to a metal or polymeric appliance or to suitable wear material by using a suitable mold to produce necessary pressure and temperature to bond the bonding material to the substrate. After the molding step the salt is leached from the materials by immersion of the prosthesis in purified water.

For molding the growth promoting material into special shapes it is preferred that the stock material be molded prior to sintering by pressure and temperatures up to 204° C. Complicated shapes can be produced to duplicate the anatomy of resected joint bone and tissue.

The stabilization of orthopedic appliances with the tissue ingrowth promoting material results from ingrowth of tissue into the material rather than by sequestration of the appliance. Actual animal implants have shown the rapid development of loose, immature collagen throughout the material (3000 $\mu$m in radial dimension) during the third, fourth and fifth weeks. At the same time dense mature collagen was seen to develop from the periphery of the implant towards the center. There is a distinct trend that the depth of mature collagen increases with time following implantation. It appears that the relatively rapid development of loose, immature collagen proceeds in situ as a direct consequence of the hematoma which was seen to develop within the implant materials at implantation.

Such animal implants resulted in linear rates of mature collagen development between 40 and 120 $\mu$m per week.

Partial and complete joint prosthesis devices are believed to be possible through the use of the improved composition of material of the present invention. The building blocks of such composite structures include the composition of material, previously described as a bonding material such as the Du Pont TEFLON FEP material, metallic prosthesis elements, and a wear material including material of Du Pont TEFLON TFE resin with inert material and fibrous material embodied herein as hereinafter described.

With those building blocks the growth promoting material of the present invention may be added to usual metal prosthetic devices for stabilization of such devices and may be used with other material for partial or total joint replacement. Typical examples of the stabilizing use of such materials would be a femoral head device with the growth promoting material bonded to he stem of a metal prosthesis. An acetabular cup prosthesis with the growth promoting material bonded to the convex side thereof would be another type of device which would be stabilized by the growth of tissue into the material bonded to the cup. Another possible use of the growth promoting material for stabilization could be in single teeth or total dentures stabilized with respect to gum tissue and mandibular hone.

A partial joint prosthesis can be accomplished on a knee by utilizing the growth promoting material positioned on the tibial plateau after the minimum necessary resection with the wear material (hereinafter described) bonded to the top of the growth promoting material by the usual bonding material. This laminated structure is secured in position in any suitable manner such as by letting the growth promoting material extend beyond the articulating surface laterally and medically for suturing at implantation. A similar implant to be femoral portion of the knee to mate with the tibial implant may be used to thereby provide a complete joint prosthesis.

With partial or complete joint prostheses it is important that the implanted device have uniform fixation, appropriate friction and wear characteristics, and approximate the bulk and strength of the resected tissue. All materials should be biocompatible, have no chemical migration when implanted and be stable for autoclaving. The composite structure for partial or complete joint prosthesis should approximate the resilience of the normal joint. Where additional resilience is desired, a layer of medical grade silicone rubber may be added between the growth material and the wear material.

Another possible human implantation use of the growth promoting material of the present invention at prosthetic tendons. For such prosthetic tendons the growth promoting material is bonded to the ends of an elongate member of suitable mechanical and surface properties of approximately the desired tendon length. A suitable construction member has been disclosed in U.S. Pat. No. 4,445,690. The growth promoting material at the ends serves to form a bond to the stump of the excised tendon close to the point at which the tendon enters the muscle at one end and to the bone at the other end.

A factor in the use of the growth promoting material which facilitates its use if it is to be bonded to other materials is to dissolve the salt in the material only in the surface to be bonded until the bonding is complete. This surface leaching has been accomplished by floating the flat material with the salt therein on distilled water for a short period of time such as twenty minutes. The bonding is then completed and any molding accomplished on the laminated structure to prepare it for implantation. When the molding is completed, the remainder of the salt is dissolved from the material.

Preferred compositions of wear materials for implantation have been described in U.S. Pat. Nos. 4,188,532 and 4,209,480. The improved growth promoting material of the present invention includes ingredients with a surface tension above $3.5 \cdot 10^{-4}$ N per centimeter on a scale extending from 2 to $8 \cdot 10^{-4}$ N per centimeter.

The foregoing disclosure and description of the invention are illustrative and explanatory thereof and various changes in the size shape and materials as well as in the details of the illustrated construction, may be made within the scope of the appended claims without departing from the spirit of the invention.

What is claimed is:

1. A biocompatible material suitable for in vivo implantation, comprising:
   fibers or particles, at least a portion of which have a critical surface tension above 35 mN/in on a scale extending from 20 to 80 mN/in; and
   a means for bonding the fibers or particles,
   wherein the bonded fibers or particles define a porous structure, the pores of which range in size from 150 $\mu$m to 300 $\mu$m, thereby imparting an enhanced tensile strength to the biocompatible material, and wherein the biocompatible material is in the form of a sheet having a thickness of 1.0 mm or less.

2. The biocompatible material of claim 1 wherein the biocompatible material is in the form of a sheet having a thickness of less than 0.8 mm.

3. The biocompatible material of claim 1 wherein the biocompatible material is in the form of a sheet having a thickness of from 0.39 mm to 0.96 mm.

4. The biocompatible material of claim 1 wherein the biocompatible material is in the form of a sheet having a thickness of from 0.4 mm to 0.5 mm.

5. The biocompatible material of claim 1 wherein the fibers or particles comprise a material selected from the group consisting of stainless steel, silicone carbide, aluminum oxide and zirconia.

6. The biocompatible material of claim 1 wherein the bonding means is a material selected from the group consisting of a fluorinated ethylenepropylene polymer, a perfluorinated polymer, a polyethylene, a polyester and a polyaramide.

7. The biocompatible material of claim 1 wherein the porous structure comprises both spheroidal and dendritic spaces that are interconnected.

8. A biocompatible laminated material comprising the biocompatible material of claim 1 and a wear material bonded to a surface of the biocompatible material.

9. The biocompatible laminated material of claim 8 wherein the wear material comprises carbon fibers and polytetrafluoroethylene resin sintered with the carbon fibers.

10. The biocompatible material of claim 1 wherein the fibers or particles comprise alumina, and the bonding means comprises polytetrafluoroethylene resin particles or fibers.

11. The biocompatible material of claim 10 wherein the volume of the alumina fibers or particles ranges from 0.5% to 2.5% of the volume of the biocompatible material, the volume of the polytetrafluoroethylene fibers ranges from 5% to 20% of the volume of the biocompatible material, and the volume of the polytetrafluoroethylene resin particles ranges from 5% to 15% of the volume of the biocompatible material.

12. The biocompatible material of claim 10 wherein the volume of the alumina fibers or particles is 1.13% of the volume of the biocompatible material, the volume of the polytetrafluoroethylene fibers is 10% of the volume of the biocompatible material, and the volume of the polytetrafluoroethylene resin particles is 8.6% of the volume of the biocompatible material.

13. The biocompatible material of claim 1 wherein the bond provided by the bonding means is at relatively small points such that substantial portions of the surface of the fibers or particles are exposed.

14. The biocompatible material of claim 1 wherein the porous structure has a void space associated therewith, and wherein the volume of the void space ranges from 70% to 82% of the volume of the biocompatible material.

15. The biocompatible material of claim 1 wherein the porous structure has a void space associated therewith, and wherein the volume of the void space ranges from 82% to 87% of the volume of the biocompatible material.

* * * * *

UNITED STATES PATENT AND TRADEMARK OFFICE
CERTIFICATE OF CORRECTION

PATENT NO.    : 6,679,913 B2
DATED         : January 20, 2004
INVENTOR(S)   : Charles Homsy It is certified that error appears in the above-identified patent and that said Letters Patent is hereby corrected as shown below:

Column 11,
Lines 63 and 64, "mN/in" should read as -- mN/m --

Signed and Sealed this

Twenty-seventh Day of July, 2004

JON W. DUDAS
*Acting Director of the United States Patent and Trademark Office*